United States Patent [19]

Coghlan

[11] 4,112,115

[45] Sep. 5, 1978

[54] THERAPY OF LEG MUSCLE CRAMPS

[76] Inventor: Charles C. Coghlan, 3358-0 Monte Hermosa, Laguna Hills, Calif. 92653

[21] Appl. No.: 740,118

[22] Filed: Nov. 8, 1976

[51] Int. Cl.² .............................................. A61K 31/27
[52] U.S. Cl. .................................................... 424/300
[58] Field of Search ............................... 424/300, 349

[56] References Cited

PUBLICATIONS

Circulation 3: 681–689 (1951).
Acta Medica Scandinavica 206-supple. 206, 196–206 (1946).
Proceedings Mayo Clinic 25: 657–659, (1950).
J.A.M.A., 150-630 (10-11-53).

*Primary Examiner*—Stanley J. Friedman
*Attorney, Agent, or Firm*—Albert M. Herzig; Edward C. Walsh

[57] ABSTRACT

Spasms in flexor and extensor muscles such as calf muscles are alleviated by topically administering to the surface of the adjacent skin a nitrite vasodilator agent, such as glyceryl trinitrate, in a suitable carrier.

10 Claims, No Drawings

THERAPY OF LEG MUSCLE CRAMPS

This invention relates to the therapy of muscle cramps as commonly occur in leg muscles, particularly calf muscles, and more particularly to such therapy with an externally applied topical agent.

It is a matter of common knowledge that cramps or spasms often occur in the flexor and extensor muscles of the leg, particularly the calf muscles. The onset is often nocturnal, and persistent and painful, and frequently encountered in those of sedentary habit and in the aged; although similar cramps often occur following extreme muscular exertion, as may happen in athletics.

Therapy of such cramps is not entirely satisfactory, such orally administered agents as calcium supplements, vitamin E, B vitamins, and the like having some value in some cases but not in others.

I have found that the external application to the skin adjacent muscles subject to cramp with a nitrite vasodilator agent in a suitable carrier provides rapid relief of cramp and indeed may be used with good results prior to the onset of such cramps when they would otherwise be anticipated. "Cramp" is here used as synonymous with "spasm".

By "nitrite vasodilator agent", I include the nitrate and nitrite compounds useful as coronary vasodilators and commonly employed orally for the treatment of myocardial insufficiency, to relieve the symptoms of angina pectoris. This class of agents includes glyceryl trinitrate, amyl nitrite, glycol dinitrate, mannitol hexanitrate, erythrityl tetranitrate, pentaerythritol tetranitrate, isosorbide dinitrate, triethanolamine trinitrate, and similar agents, all of which are believed to exert a vasodilatory action by releasing nitrite ions. Even those which are nitrates are commonly referred by the term already given, i.e. nitrite vasodilator agents, as mentioned for example in the text: T. Sollman — A Manual of Pharmacology, Ed. 6, Philadelphia and London, 1942, page 514.

Agents of the type described have been employed topically for the treatment of peripheral vascular disorders, viz., Raynaud's disease, as shown in the following papers: *Acta Medica Scandinavica* 206 — supplement 206, 196–206 — Lund (1946), *Proceedings Mayo Clinic* 25: 657–659 (1950) and *Circulation* 3: 681–689 (1951).

Glyceryl trinitrate has been recommended for the treatment of night cramps in the legs by sublingual administration, precisely as used for the treatment of angina, in a letter to the *Journal of the Americal Medical Association* 150: 630 (Oct. 11, 1953).

Generally speaking, and in accordance with an illustrative embodiment of my invention, I use a solution of a selected nitrite vasodilator agent, or mixture of one or more such agents, for which I prefer and find best glyceryl trinitrate, in a pharmacologically acceptable carrier, for which I prefer a liquid in which said agent is soluble, and for which I prefer aqueous ethanol or aqueous isopropanol, preferably of from about 50% by volume to about 85% by volume of the selected alcohol. The nitrite vasodilator agent may be present at a concentration of from about 0.5 to about 5 grams/100 cc. I prefer and find best a concentration of 1 gram/100 cc, i.e. 1% w/v.

The formulations known as rubbing alcohol, consisting essentially of 70% by volume aqueous ethanol or aqueous isopropanol, are convenient liquid vehicles. Other agents may be present as well, such as 1 to 2% methylsalicylate, 1 to 2% menthol, and the like. Thus, a typical formulation is:

Glyceryl trinitrate — 1 gm
Methyl salicylate — 1 gm
70% aqueous ethanol, q.s. ad 100 cc.

The selected solution is applied by topically administering to the surface of the skin adjacent a muscle in spasm or susceptible of spasm, the selected solution, as for example, that given above, as by rubbing, or by applying gauze soaked in the solution.

The amount of the solution to be used in accordance with the invention is subject to some variation in individual cases, as indeed is the case rather generally with topical medication. However, a few cubic centimeters, such as 4 or 5 cc of a 1% solution, rubbed into the skin are generally adequate to obtain the desired relief, and in most cases need not be repeated until the next day. Frequently, application of a quantity of the solution sufficient to relieve the muscle spasm in quite generally substantially less than the quantity required to bring on the headache commonly associated with overdosage of nitrite vasodilator agents, in particular glyceryltrinitrate.

While I have illustrated my invention in terms of a liquid solution, I contemplate the use of carriers other than solutions as this term is commonly understood. Thus, a vanishing cream base, or hydrophilic ointment USP, or Simple Cream, British Pharmacopoeia, and similar unguent carriers may be used instead of aqueous alcohol. Even in such semi-solid carriers the nitrite vasodilator agent is generally in true solution in one or more phases of the carrier. Thus, the recitation "a solution of a nitrite vasodilator agent in a pharmacologically acceptable carrier" is intended to include all of the foregoing illustrative embodiments.

While I have described my invention with the aid of numerous specific examples, it will be recognized by those skilled in the art that many variations are possible without departing from the spirit and scope of the invention.

Having described the invention I claim:

1. A method of alleviating spasms in flexor and extensor muscles comprising the step of topically administering to the surface of the skin adjacent said muscle a spasms alleviating amount of a solution of a nitrite vasodilator agent in a pharmacologically acceptable carrier.

2. The method in accordance with claim 1 wherein said nitrite vasodilator agent is selected from the group consisting of glyceryl trinitrate, amyl nitrite, glycol dinitrate, mannitol hexanitrate, erythrityl tetranitrate, pentaerythritol tetranitrate, isosorbide dinitrate, triethanolamine trinitrate and mixtures thereof.

3. The method in accordance with claim 1 wherein said carrier is selected from the group consisting of aqueous ethanol and aqueous isopropanol.

4. The method in accordance with claim 3 in which said carrier liquid consists from about 50% by volume to about 85% by volume of said ethanol or isopropanol.

5. The method in accordance with claim 1 wherein said nitrite vasodilator agent is glyceryl trinitrate.

6. The method in accordance with claim 1 wherein said nitrite vasodilator agent is present in said carrier at a concentration of from about 0.5 to about 5 grams per 100 cc.

7. The method in accordance with claim 4 wherein the nitrite vasodilator is glyceryl trinitrate.

8. The method in accordance with claim 6 wherein the nitrite vasodilator is glyceryl trinitrate and the carrier liquid consists of from about 50% by volume to about 85% by volume of alcohol in aqueous ethanol or aqueous isopropanol.

9. The method in accordance with claim 1 wherein the solution of a nitrite vasodilator consists of 1 gram glyceryl trinitrate, 1 gram methylsalicylate and enough 70% aqueous ethanol to make 100 cc. of solution.

10. The method in accordance with claim 1 wherein the nitrite vasodilator agent is present at a concentration of 1 gram/100 cc.

* * * * *